(12) United States Patent
Prescott (10) Patent No.: US 7,901,351 B2
(45) Date of Patent: Mar. 8, 2011

(54) FIBEROPTIC OTOSCOPE SYSTEM

(75) Inventor: James T. Prescott, McPherson, KS (US)

(73) Assignee: Medical Innovations, LLC, McPherson, KS (US)

( * ) Notice: Subject to any disclaimer, the term of this patent is extended or adjusted under 35 U.S.C. 154(b) by 1342 days.

(21) Appl. No.: 10/818,768

(22) Filed: Apr. 6, 2004

(65) Prior Publication Data

US 2005/0143626 A1 Jun. 30, 2005

Related U.S. Application Data (60) Provisional application No. 60/532,468, filed on Dec. 24, 2003, provisional application No. 60/559,223, filed on Apr. 2, 2004.

(51) Int. Cl.
*A61B 1/06* (2006.01)
(52) U.S. Cl. .......... 600/162; 600/178; 600/182; 600/200
(58) Field of Classification Search .................... 600/200
See application file for complete search history.

(56) References Cited

U.S. PATENT DOCUMENTS

| | | | | |
|---|---|---|---|---|
| 3,067,648 A * | 12/1962 | Cohen | ........................ | 351/218 |
| 3,848,587 A | 11/1974 | McDonald | | |
| 4,335,713 A * | 6/1982 | Komiya | ........................ | 600/114 |
| 5,177,424 A | 1/1993 | Connors | | |
| 5,868,665 A * | 2/1999 | Biggs | ........................ | 600/112 |
| 5,919,130 A | 7/1999 | Monroe et al. | | |
| 5,935,058 A * | 8/1999 | Makita et al. | .................. | 600/200 |
| 5,960,145 A | 9/1999 | Sanchez | | |
| 5,961,441 A | 10/1999 | Plumb et al. | | |
| 6,306,084 B1 * | 10/2001 | Pinczower | .................... | 600/184 |
| 6,416,464 B2 | 7/2002 | Elliott | | |
| 6,699,178 B1 | 3/2004 | Koda | | |
| 6,817,976 B2 * | 11/2004 | Rovegno | ........................ | 600/173 |
| 6,863,651 B2 * | 3/2005 | Remijan et al. | ................ | 600/130 |
| 2002/0038075 A1 | 3/2002 | Tsai | | |

* cited by examiner

*Primary Examiner* — Matthew J Kasztejna
(74) *Attorney, Agent, or Firm* — Karen A. Rex; Sherman D. Pernia (57) ABSTRACT

The present optical image viewing fiberoptic otoscope electromagnetically passive. A body portion is connectable to a light source and has mounted to it a fiberoptic cable and an optical viewer. The fiberoptic cable is thin and flexible, and contains separate light and image transmission paths. Its distal end is adapted for emitting and receiving light. The body includes a light source connection for interfacing an external light source. An optical-type image viewer attached to the body is in light communication with the image path for displaying a received image for viewing by a user. One or more tools are mountable to the otoscope body or fiberoptic cable for performing an operation at the distal end of the fiberoptic cable, e.g., removal of a material from the site. Optionally, the otoscope body may be mounted to a headband via an articulated support arm.

19 Claims, 10 Drawing Sheets

FIBEROPTIC OTOSCOPE SYSTEM

The present application claims the benefit of prior filed U.S. Provisional Application Ser. No. 60/532,468 filed 24 Dec. 2003 and to new U.S. Provisional application Ser. No. 60/559,223 filed 2 Apr. 2004, to which prior applications the present application is a regular U.S. national application.

FIELD OF THE INVENTION

The present invention is in the field of medical instruments useful for illuminating, viewing, diagnosing and removing material from the ear, nose and throat. More specifically, the present invention relates to otoscopes having fiberoptic imaging and illuminating means, and further means for engaging and removing foreign objects or materials.

BACKGROUND OF THE INVENTION

A physician's usage of the typical otoscope to perform a diagnostic inspection of a patient's tympanic membrane can be frustrated due to a variety of causes. These include narrow ear canals, excess cerumen and hair that can block the physician's view of the tympanic membrane. With many children, as with some adults, the prospect of the physician forcibly invading the patient's personal space as well as the external auditory canal is very disconcerting to the patient. This apprehension can cause seriously disruptive behavior, especially in child patients. It is additionally traumatizing, both physically and emotionally, to small children (and some adults) to have to blindly scrape cerumen out of their external auditory canals in order to simply inspect the ear canal and tympanum. Cerumen serves a purpose and unless it is causing diminished hearing it should be left alone.

The field has recognized these problems and has been motivated to seek solutions. For example, Krug et al. (U.S. Pat. No. 5,209,757) disclose an illuminated ear cleaning device. The Krug device comprises a small lamp in proximity with retrieval tool (ear wax loop) at the end of a probe. The lamp illuminates the point of use and a magnifying lens provided at the base of the probe is focused at the point of use to improve viewing the site. However, the Krug device requires that a user be in very close proximity of the patient being examined. Elliott (U.S. Pat. No. 6,416,464) discloses an effort to provide a variety of attachments for use with an existing otoscope. The Elliott attachments provide a variety of means for inspecting an ear or a nose and removing foreign material therefrom. The Elliott device, like the Krug device, requires that a user be in very close proximity of the patient being examined. Unlike the Krug device, the Elliot system does not provide a source of illumination proximate the site under examination.

Recently, Koda (U.S. Pat. No. 6,699,178) disclosed a self-contained endoscopic auditory canal cleaning apparatus. The Koda apparatus is self-contained in that it included an active electrical power supply and associated circuits. The Koda apparatus comprises an internally illuminated ear-pick made of a light passing material and held in a hollow holding part. The ear-pick and hollow holding part combination is rotatable around a separate fiberscope imaging cable. Diffused light emitted from the ear-pick is used to illuminate the auditory canal and the fiberscope is used to capture images and send them to a display device. The display device has an eyepiece part and a main body. The eyepiece part comprises a simple convex lens to match the fiberscope to the eyepiece part. The display device also comprises a battery power supply and associated light source circuitry.

Although the above devices and other in the field may be useful for their intended purposes, it would still be beneficial to the field to have an alternative otoscope that can directly illuminate and image the tympanum without violating a patient's comfort zone. It would also be beneficial if the device could easily be adapted to remove material or foreign objects from the auditory canal as well. It would be additionally beneficial if the otoscope was passive, in that it contained no para-magnetic and generated no electric fields, allowing it to be used in otherwise restrictive environments (e.g., in proximity to an MRI machine or in an oxygen rich atmosphere). It would be further beneficial to have such a fiberoptic otoscope device that directly interfaced with existing light sources, such as the Welch Allyn otoscope handle.

SUMMARY OF THE INVENTION

The present invention is a passive optical image viewing fiberoptic otoscope. The present otoscope is passive in that it generates no electric fields in a preferred embodiment can be made of non para-magnetic materials. The present optical fiberoptic otoscope comprises an otoscope body which interfaces with a flexible solid fiberoptic cable of very small diameter, and with an achromatic optical image viewer having an achromatic lens system providing a chromatically correct optical image. Light is provided to the device via a light source connector attached to the otoscope body. In a preferred embodiment, the light source connector is adapted to attach to a Welch Allyn brand light source (e.g., 71000 series power handles, Welch Allyn, Inc., Skaneateles Falls, N.Y.), but can be adapted to attach to an ambient light source collector.

The otoscope body of the present optical image viewing fiberoptic otoscope has a cable end, a viewer end and a mid-section, and has an interior passage connecting the cable end with the viewer end. An intersecting passage connects the mid-section of the otoscope body to the interior passage. At its proximal end, the flexible solid fiberoptic cable is received within the interior passage and extends out from the cable end of the otoscope body. The solid fiberoptic cable has a plurality of optical fibers for conducting light and is "solid" in that the optical fibers are tightly packed together in the cable. The achromatic optical image viewer is attached to the viewer end of the otoscope body and in communication with the interior passage. The light source connector is attached to the mid-section of the otoscope body and is in communication with the intersecting passage.

In a preferred embodiment, the distal end of the imaging path of the fiberoptic cable has a duel lens system which provided achromatic correction. The distal lens system provided red, green, blue correction and flatten image field and was encased in a first stainless steel cylinder (~1.1 mm long). This distal lens system allowed a field of view of about 60 to 65 degrees. If a single distal lens is used, the first stainless cylinder in not necessary. A fiberoptic image conduit formed the imaging path of the fiberoptic cable, and butted up against the distal lens system. The two were encased by a stainless cylinder (~3.2 mm long) at the distal end. The image conduit, manufactured by Fujikura, was 0.7 mm in diameter and contains 15 thousand individual strands of fused silica. These strands are coherent which means that they lie perfectly in place along the entire length of the strand. Coherency is important to proper image transfer.

In a preferred embodiment, the proximal end of the image conduit abutted against a dual achromatic lens complex of a Hastings triplet lens system. This lens complex provided appropriate color correction of the image. Generally, color correction is necessary to offset any prism effect of the lenses at the distal end. Without this correction color could be altered and medical diagnosis impaired. The achromatic lens complex of the Hastings lens system also provided for magnification of the image, and the Hastings system itself provides inversion of the image back to its upright orientation to correct for the initial image inversion which occurred at the distal end lens. The viewer's subsequent eyepiece lens (of the Hastings system) presents the now magnified and upright image for viewing.

Surrounding the fused image conduit are numerous extremely small and flexible light conduits which form the light path. The image conduit and surrounding light conduits extend from the tip of the distal end of the fiberoptic cable back through the cable end of the otoscope body and into the interior passage. Within the interior passage the image path and the light path diverge from each other. The image path proceeds through the interior passage to communicate with the achromatic lens complex. The light path diverges from the image conduit to proceeds through the intersecting passage to the light source connection. At the light source connection, the light path with its plurality of light conduits terminates in a light path interface where it receives illuminating light from an external light source. The exterior surface of the light path surrounding the image path is tightly encased in a polyamide coating. This is a standard coating utilized on medical grade endoscope cables and allows for the use of common sterilization and disinfectant techniques as used for other endoscopes. A preferred embodiment of the present fiberoptic otoscope has a fiberoptic cable with a working length of about 14 inches and has a cable diameter of about 1.3 to 1.5 millimeters depending on the number of light conduits incorporated.

An adjustable "ear stop" slides over the distal end and functions as a contact point for the fingers as well as a safety stop that prevents contact with the tympanic membrane. Other features that have been incorporated in the ear stop, such as an attachment for removal of ear wax with an ear loop and a channel that allows for attachment of an alligator for retrieval of foreign bodies from the nose or ear. The present fiberoptic otoscope system can directly illuminate and image the tympanum with a greatly reduced possibility of violating a patient's comfort zone. Also, the present fiberoptic otoscope can be easily adapted to remove material or foreign objects from the auditory canal using a variety of ancillary attachments. Additionally, the present otoscope is passive, in that it contains no para-magnetic materials and generates no electric fields. Further, the present fiberoptic otoscope device is adaptable to directly interfaced with existing light sources via either a direct attachment (e.g., see U.S. Pat. No. 5,177,424), via a remote attachment, or via an ambient light collecting device.

DETAILED DESCRIPTION OF THE INVENTION

Referring now to the drawings, the details of preferred embodiments of the present invention are graphically and schematically illustrated. Like elements in the drawings are represented by like numbers, and any similar elements are represented by like numbers with a different lower case letter suffix.

Figure 1A:
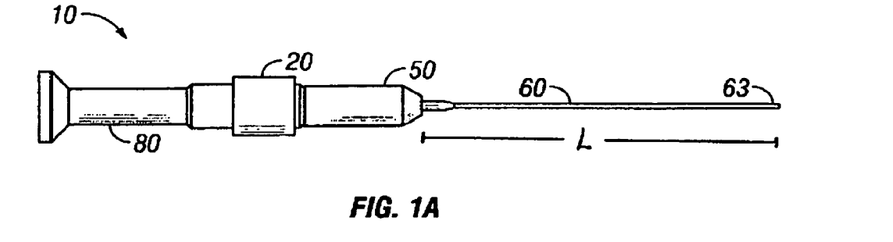
FIG. 1A is a top plan view of an exemplary fiberoptic otoscope of the present invention.
Figure 1B:
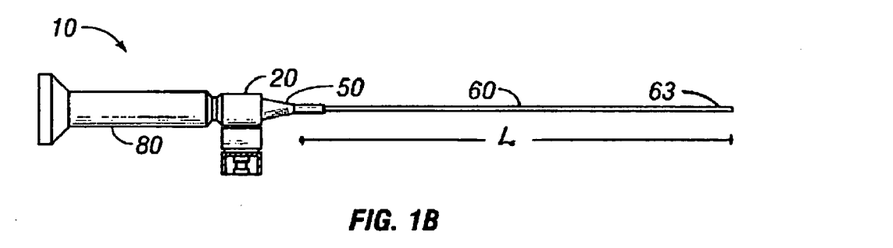
FIG. 1B is a side elevation and partial cross-sectional view of an exemplary fiberoptic otoscope of the present invention.
Figure 1C:
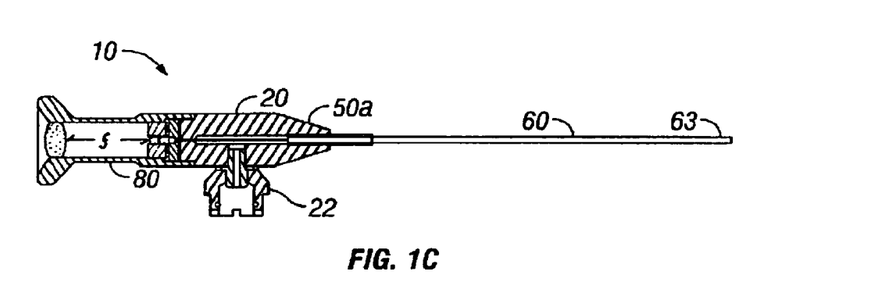
FIG. 1C is a side elevation, cross-sectional view of an exemplary fiberoptic otoscope of the present invention.

The present invention is an optical image viewing fiberoptic otoscope 10 as generally illustrated in the figures. The present otoscope is "optical" image viewing in that the user views an optical presentation of a light image through a lens, as opposed to viewing a digital representation of the image reproduced on a view screen. As exemplified in FIGS. 1A to 1C, the main components of the present fiberoptic otoscope 10 include a fiberoptic otoscope body 20, a flexible fiberoptic cable speculum 60 and cable head 50, and an optical image viewer 80. The present invention utilizes existing fiberoptic technologies and incorporates them into a novel optical image viewing otoscope 10. Additionally, the present fiberoptic otoscope 10 includes a tool 104 for performing some operation at the site of the distal end 63 of the fiberoptic cable 60. The tool 104 can be integral to the fiberoptic otoscope body 20 or can be separately mountable on the fiberoptic cable speculum 60.

In practicing the invention, the fiber optic cable head 50 serves as an attachment means for connecting the fiberoptic speculum 60 to the otoscope body 20. The fiberoptic cable/speculum 60 is flexible over a sufficient length, and has a first or proximal end 62 (see FIG. 2B) and a second or distal end 63. The proximal end 62 passes through and is held/supported by the fiberoptic cable head 50. The second distal end 63 of the optical cable 60 is adapted for emitting and receiving light. The speculum cable 60 itself comprises light conduits of two types/purposes: light emitting 66 and image (received light) transmitting 68, in other words, a light emitting path 66 and a light image receiving path 68. The fiberoptic otoscope body 20 has the cable head 50a attached to it at one end and an optical image viewer 80 attached to it at the other end. The otoscope body 50 houses a light source interface 22 and a received image interface 84. The optical image viewer 80 attaches to the otoscope body 20 and provides the mechanism for displaying a received light image for optical viewing by a user.

Figure 2A:
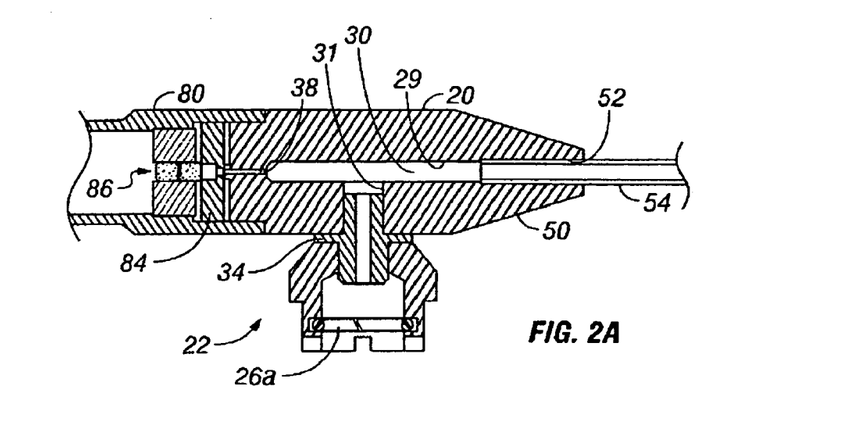
FIG. 2A is a side elevation cross-sectional view of an example of an otoscope body and cable head combination of the present invention shown without the fiberoptic cable components.

As shown in the embodiment exemplified in FIG. 2A the cable head 50 can be integral with the otoscope body 20 of the optical image viewing fiberoptic otoscope 10. Alternatively, as exemplified in FIG. 2B, the cable head 50a can be a completely separate component that is attachable to the otoscope body 20. Generally, the present otoscope body 20 has a manifold chamber 30 comprising the interior passage 29 and the intersecting passage 31 (see FIG. 2A). Within the manifold chamber 30, the proximal end 62 of the fiberoptic cable 60 terminates and the light emitting path 66 and image receiving path 68 are separated from one another and separately routed to their respective proximal terminal interfaces. At one end, the interior passage 29 communicates with the cable receiver bore 52 of the cable head 50. The cable receiver 52 receives, holds and supports the proximal end 62 of the speculum cable 60, allowing the light and image paths 66 & 68 to pass through to the manifold chamber 30. In the preferred embodiment exemplified, the cable head 50 included a cable support 54 at least partially received into the cable receiver bore 52 through which the optical cable 60 also passed. The cable support 54 provided mechanical support for the optic cable 60 at the point it entered the cable head 50.

Figure 2B:
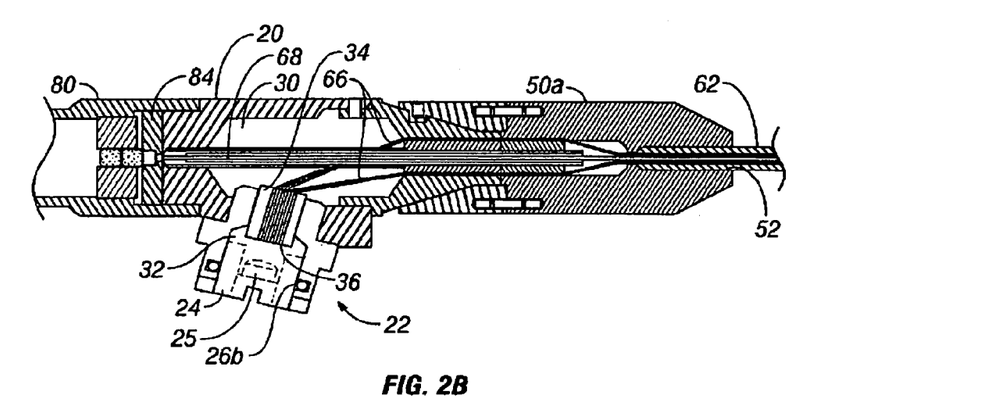
FIG. 2B is a side elevation cross-sectional view of an example of an alternative otoscope body and cable head combination of the present invention showing the fiberoptic components of the cable in place.

The fiberoptic otoscope body 20 has a light conduit receptacle 34 for holding and terminating the proximal end of the light emitting path 66 and an image conduit receptacle 38 for terminating the proximal end of the image receiving path 68. As shown in FIGS. 2A and 2B, the light conduit receptacle 34 is disposed in a light source adapter 22. The adapter 22 provides an attachment means for removably connecting a light source 24 to the otoscope body 20. In a preferred embodiment, the adapter 22 provided for attaching a typical Welch-Allyn type otoscope light source to the present fiberoptic otoscope 10, however, the adapter 22 can be configured to connect to any of the other such light sources available by the ordinary skilled artisan. The adapter 22 practiced in the figures included a detent mechanism 26 for releaseably attaching the light source 24 to the adapter 22 of the otoscope body 20. In this embodiment, the detent mechanism 26 comprised a retained lock ring 26a on the adapter 22 that engaged a detent groove 26b on the light source 24. Other mechanisms for attaching a light source 24 to the present fiberoptic otoscope 10 are known to and adaptable by one of ordinary skill in the art for practice in the present invention.

The light source 24 provides light to the light chamber 32 of the adapter 22. The light conduit interface 36 at the proximal end of the light emitting path 66 is received in the light conduit receptacle 34 of the light source adapter 22. The light conduit receptacle 34 holds the light conduit end(s) in a disposition to allow light from the light chamber (see FIG. 2B) to enter the light transmission path at the light conduit interface 36. In a preferred embodiment, the bulb/emitter 25 of a light source 24 flooded the light chamber 32 with light. Light from the chamber 32 passes via the light path interface 36 into the the light emitting path 66. In a preferred embodiment, the light source 24 was detachable from the otoscope body 20. However, it is intended that the present fiberoptic otoscope 10 optionally may include the light source 24 as a component part. Further, it is intended that the optional light source 24 may include an electrical power source as well.

Figure 3:
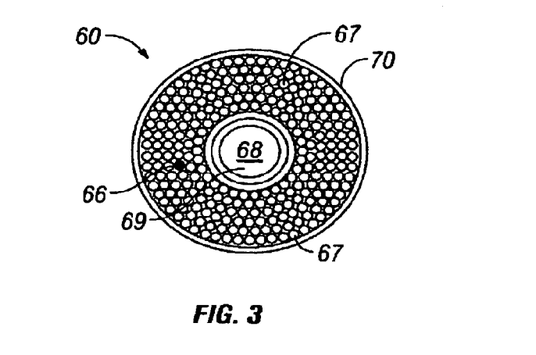
FIG. 3 is a cross-sectional view through the axis of the optic cable of the present invention showing a central image path and surrounded by a light path comprised of a plurality of light conduits.

In a preferred embodiment exemplified in FIG. 3, the fiberoptic cable speculum 60 in cross-section comprised a central image path 68 running along the axial core of the cable 60, with the image path 68 surrounded by the light emitting path 66. The image path 68 in this embodiment comprised a single image conduit 69, while the light path 66 comprised a plurality of light conduits 67. The exemplified embodiment had a plurality of individual light conduits 67 in the light path 66. The image conduit 69 and the light conduits 67 practiced in this embodiment were obtained commercially (by Myriad Fiber Imaging Tech., Inc., Mass.). However, the ordinary skilled artisan in this field can select and practice alternative image and light conduits and alternative cross-sectional configurations. That is, the number and diameter of the light conduits 67 can be varied, as well as that of the image conduit 69.

Figure 4:
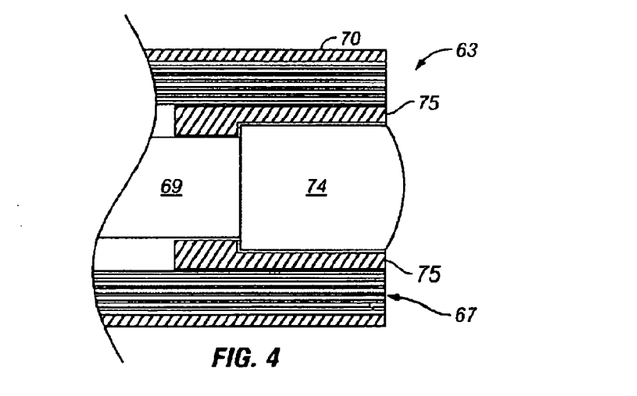
FIG. 4 is a partial cross-section illustrating an embodiment of the distal end of the fiberoptic cable of the present otoscope.

As exemplified in FIG. 4, the image conduit 69 at the distal end 63 of the fiberoptic cable 60 is terminated in a light gathering lens 74 or lenses 74 if desired. In preferred embodiments, both a gradient index lens and a dual achromaticlens complex have been successfully applied as the light gathering lens 74 to terminate the fiberoptic cable 60. The gathering lens 74 served as an image interface with the environment being viewed and increased the amount of reflected (image) light entering the image conduit 69. A lens collar 75 was used to fix the light gathering lens 74 to the distal end of the light conduit 69. The distal ends of the light conduits 67 and the cable sheath 70 terminated in substantially the same cross-sectional plane as the gathering lens 74. Optionally, a disposable, optically plane lens protector sleeve (not shown) can be used to cover the distal end of the cable speculum 60 and preventing the speculum 60 from coming directly in contact with a patient during use. Alternatively, the cable 60 itself or the cable distal end 63 of the cable 60 can be made a material that can be readily disinfected or disposable.

In the embodiment exemplified, the fiberoptic cable 60 had a sheath 70 encasing the light and image paths 66 & 68, and had a length L of about 14 inches extending from the cable head 50. The composition material and thickness of the sheath 70 and this length L allowed the cable 60 to be easily looped back on itself and allowed the user to be removed (not have to hover in very close proximity) from the patient being examined. It is a specific benefit of having a length of flexible cable 60 that allows the present otoscope to be used with patients (especially children) that often are not cooperative during the very close proximity of the user during an examination. The use of a rigid speculum of similar length is both awkward for the user and risky for an uncooperative patient. Other lengths and sheath compositions are known to and selectable by one of ordinary skill in the art for practice in the present fiberoptic otoscope 10, depending, for example, on the desired flexibility and degree of removal between patient and user. Optionally, some portion of the sheath 70 (e.g., proximate its distal end 63) may be of a semi-rigid or a malleable material, which can be bent to a configuration conforming to a specific use or path it is intended to travel.

It is anticipated that the fiberoptic cable speculum 60 has a length L of at least about 0.5 cm. Operationally, maximum length is expected to depend primarily on light loss from the light and image paths causing unacceptable degradation of image quality. The outside diameter (OD) of the optic cable 60 depends in part on the desired specific flexibility and its cross-sectional configuration. In the embodiment exemplified, the OD of the speculum cable 60 was about 1.3 mm, but for otoscopic applications the speculum cable 60 could have any OD useful in the field. However, it is an intended benefit of the present otoscope 10 that the fiberoptic cable 60 have a diameter sufficiently small to pass around an obstruction in a patient's ear. Other uses for the present fiberoptic otoscope are intended, such as nasal and laryngeal applications. These and still other application may be accomplished with minimal experimentation to adapt the present fiberoptic device 10 to these other uses.

The end of the image path 68 at the proximal end 62 of the optic cable 60 is received in the image conduit bore 38 at the viewer end of the interior passage 29 of the manifold chamber 30. The proximal end of the image conduit 69 of the image path 68 terminates at the image viewer interface 84, with the proximal end of the image receiving path 66 disposed at the end of the image conduit bore 38 distal from the manifold chamber 30. See FIGS. 2A and 2B.

Figure 5:
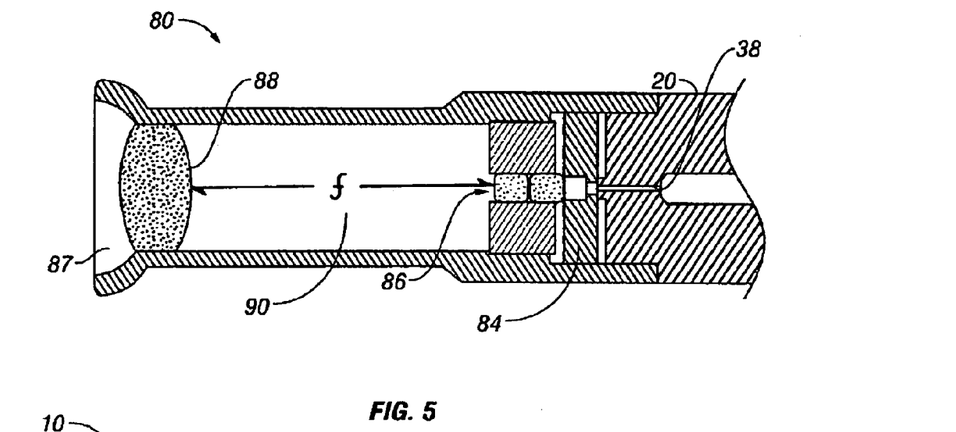
FIG. 5 is a cross-sectional side elevation view of the image viewer of the present otoscope.

As illustrated in FIG. 5, the optical image viewer 80 attaches to and extends from the back of the otoscope body 20. The image viewer 80 comprises an image viewer interface 84, followed by an achromatic projection lens assembly 86 and then an eye piece 87 and eyepiece lens 88 as an assembly. The user of the fiberoptic otoscope 10 views the image via the eyepiece lens 88. The image viewer interface 84 serves at least in part as a spacer having a central aperture through which the image from the image conduit 69 expands as it is projected onto the projection lens assembly 86. In the embodiment exemplified in the figures, the projection lens assembly 86 comprised an achromatic lens pair which corrected the color quality of the projected image and provided image magnification. The color corrected image was then projected on to the eyepiece lens 88 of the image viewer 80. A focal chamber 90 is disposed between the projection lens assembly 86 and the eyepiece lens 88. The length of the focal chamber 90 defines the focal length f of the lens system of the image viewer 80 and is selected to invert and provide a focused upright image at the eyepiece lens 88. Optionally, the focal length f is adjustable to allow focusing the image projected onto the eyepiece lens 88 to accommodate the vision correction that may be required for different users.

Figure 6A:
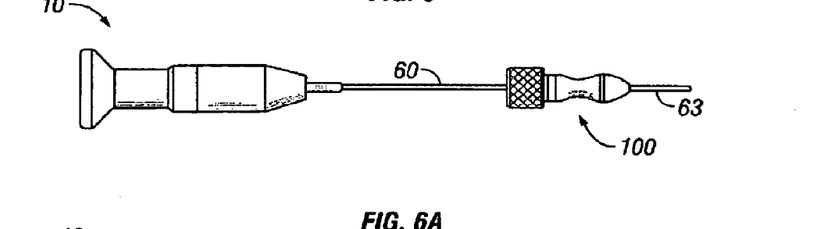
FIG. 6A is a top plan view of present fiberoptic otoscope showing a handle/stop proximate the distal end of the fiberoptic cable speculum.
Figure 6B:
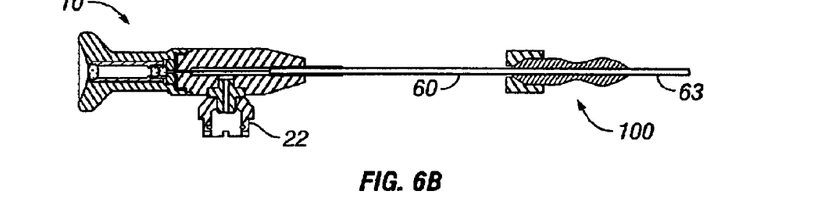
FIG. 6B is a cross-sectional side view of present fiberoptic otoscope showing a handle/stop proximate the distal end of the fiberoptic cable speculum.
Figure 7A:
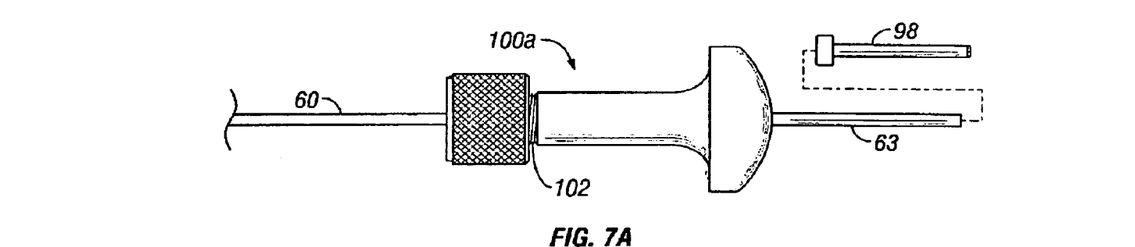
FIG. 7A is a plan view of the distal end of a fiberoptic speculum of the present otoscope showing an alternative configuration of a handle/stop installed proximate the distal end of the fiberoptic cable speculum.
Figure 7B:
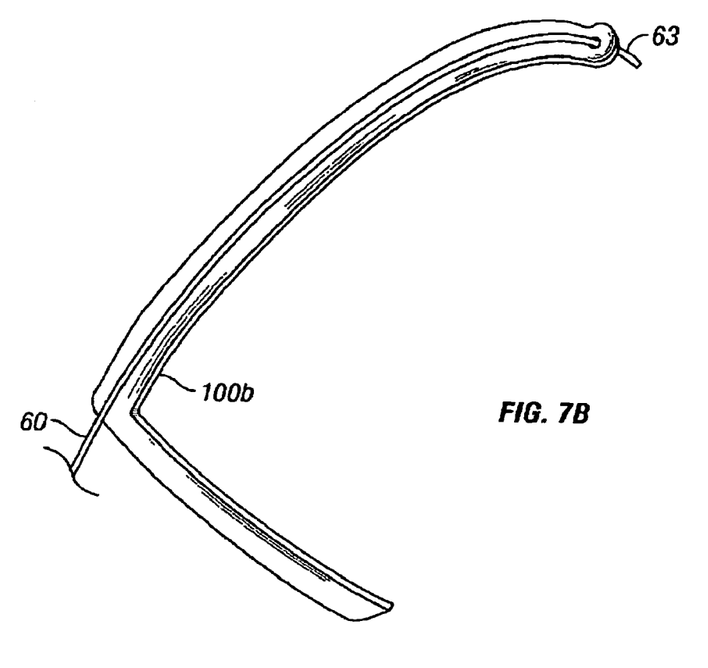
FIG. 7B is a perspective view of a further alternative handle/stop with the distal end of a fiberoptic speculum of the present otoscope.

As exemplified in FIGS. 6A and 6B, the fiberoptic cable speculum 60 of the present fiberoptic otoscope 10 preferably has a combination handle/stop 100 installed proximate the distal end 63 of the fiberoptic cable 60. In the embodiment exemplified in the figures, the handle/stop 100 had a central passage through which the cable speculum was slidably passed. The handle/stop 100 included a releaseable screw clamp mechanism 102 that was set to grip the cable 60 at a desired position and hold the handle/stop 100 in place. The handle/stop 100 was then used to facilitate manually manipulating the distal end 63 of the fiberoptic speculum 60 by the user. Further, the handle stop 100 prevented the speculum from being inserted too far into the space being observed (i.e., a patient's ear canal). Optionally, an optically neutral septum 98 can be used to provide a removable or disposable cover for the distal end 63 to protect the distal lens 74. Other configurations of handle/stops and releaseable clamp mechanisms are selectable by one of ordinary skill in the art for practice in the present invention 10 as preferred by the user or for other applications. For example, FIGS. 7A and 7B illustrate examples of an alternative configurations for handle/stops 100a & 100b. The handle/stop 100b exemplified in FIG. 7B could be used in the present fiberoptic otoscope 10 for laryngeal inspections, and could be especially useful with the handle/stop 100b being made of a malleable material. A malleable material allows the configuration of the handle/stop 100b to be adjusted by bending it to better conform with the anatomy of the patient being inspected.

Figure 8A:
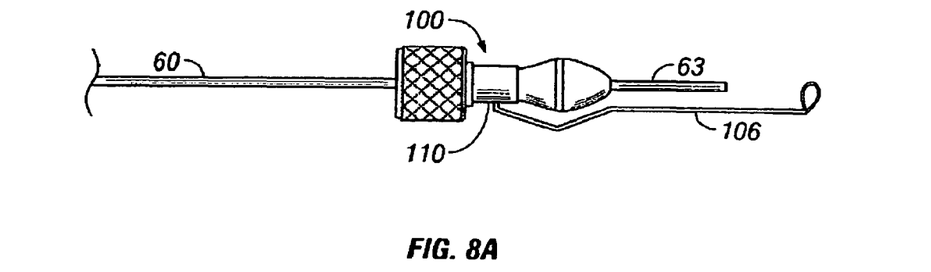
FIG. 8A is an illustration of the distal end of a fiberoptic speculum of the present invention with a handle/stop and tool combination installed proximate the distal end of the fiberoptic cable speculum.
Figure 8B:
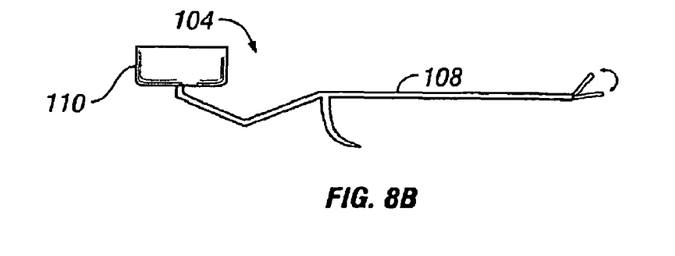
FIG. 8B is an illustration of an example of an alternative tool and clip means for attaching it to a handle/stop the present invention.

As noted above, the present fiberoptic otoscope 10 includes a tool 104 for performing some operation at the site of the distal end 63 of the fiberoptic cable 60. FIGS. 8A and 8B illustrate a tool 104 that is separable from the rest of the present fiberoptic otoscope 10 and mountable to the handle/stop 100. FIG. 8A is an example of a wire loop-type retrieval tool 106 which mounts on the handle/stop 100 and extends beyond the end 63 of the fiberoptic speculum 60 to allow a user of the otoscope 10 to both locate and remove wax from a patient's ear. The loop-type retrieval tool 106 mounts on the handle/stop 100 of the present fiberoptic speculum 60 using a snap-clip attachment means 110. Other tools useful for practice with the present fiberoptic otoscope 10 in a similar manner are known to and selectable by the ordinary skilled artisan. For example, FIG. 8B illustrates adaptation of a known tool 108 with a snap-clip attachment means 110 for mounting on the handle/stop 100 of the present fiberoptic speculum 60.

Figure 9A:
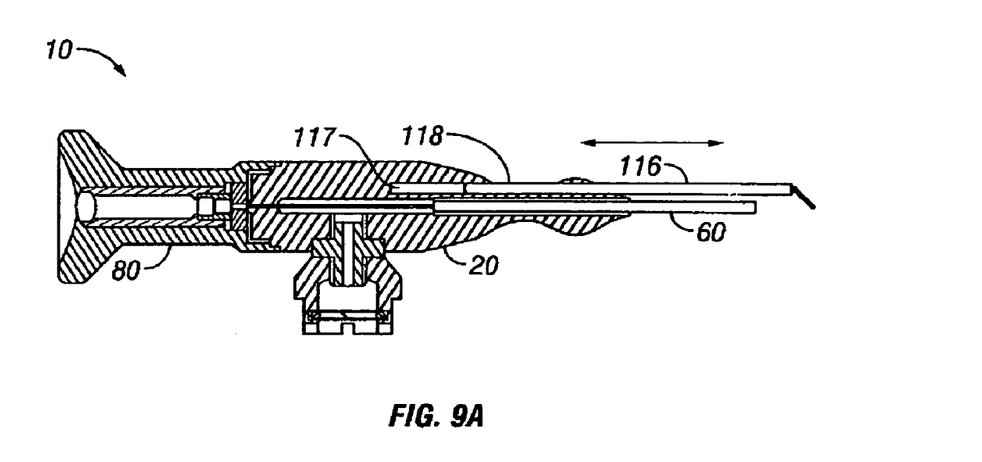
FIG. 9A is a partial cross-sectional side view of the present fiberoptic otoscope illustrating a retrieval tool (a loop) integral with the otoscope body.
Figure 9B:
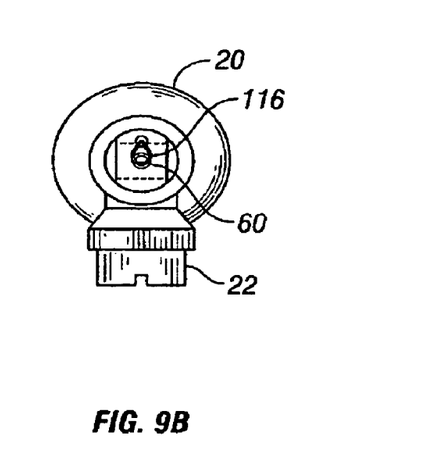
FIG. 9B is a front elevation view of the fiberoptic otoscope body of FIG. 9A.
Figure 9C:
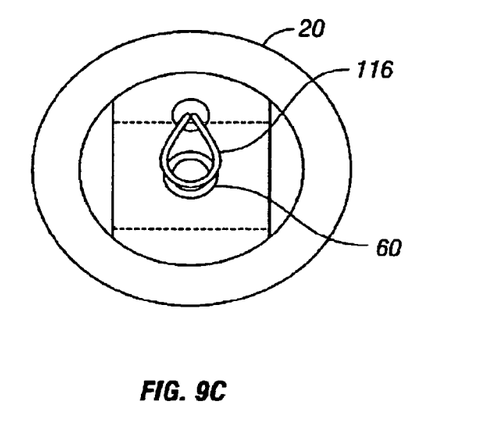
FIG. 9C is an enlarged representation of a portion of the front elevation view of the fiberoptic otoscope body of FIG. 9B.
Figure 10:
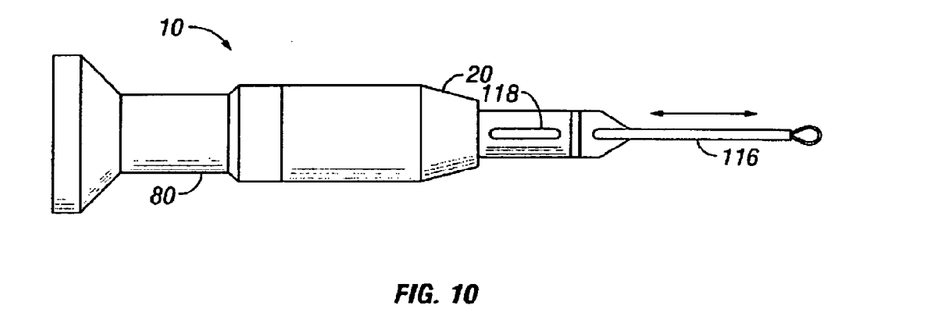
FIG. 10 is a top plan view of the present fiberoptic otoscope illustrating a retrieval tool (a loop) integral with the otoscope body.

Otoscopic retrieval tools are particularly useful in the field of otolaryngology and the present invention 10 is easily adapted to incorporate such tools 104. FIGS. 9A to 9C exemplify the present fiberoptic otoscope 10 adapted to include a loop-type retrieval tool 116 integral with the otoscope body 20. The retrieval tool 116 is received into a tool bore 117, and is manually positionable by means of a touch access 118. The touch access 118 allows the loop retrieval tool 116 to be extended over a short range (e.g., about 0.5 inch) and to be rotatable about its axis (see FIG. 10).

Figure 11A:
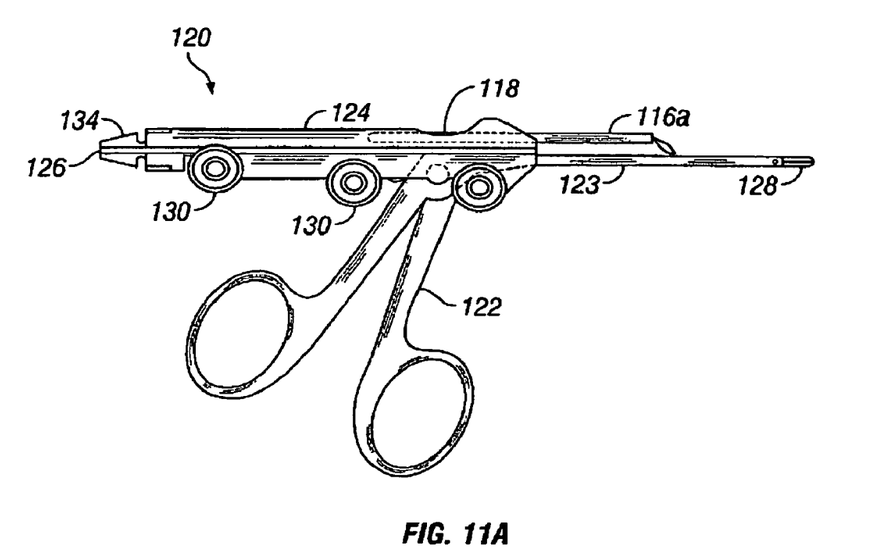
FIGS. 11A and 11B respectively are a side elevation view and a front elevation view illustrating a combination grab-type and loop-type retrieval tool mountable on the fiberoptic cable of the present invention separate from the otoscope body.
Figure 11B:
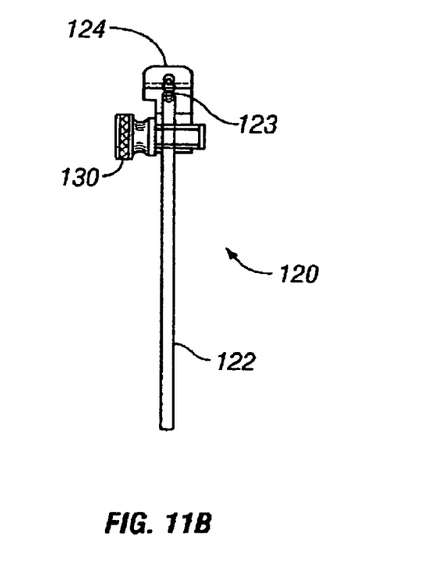
Figure 11C:
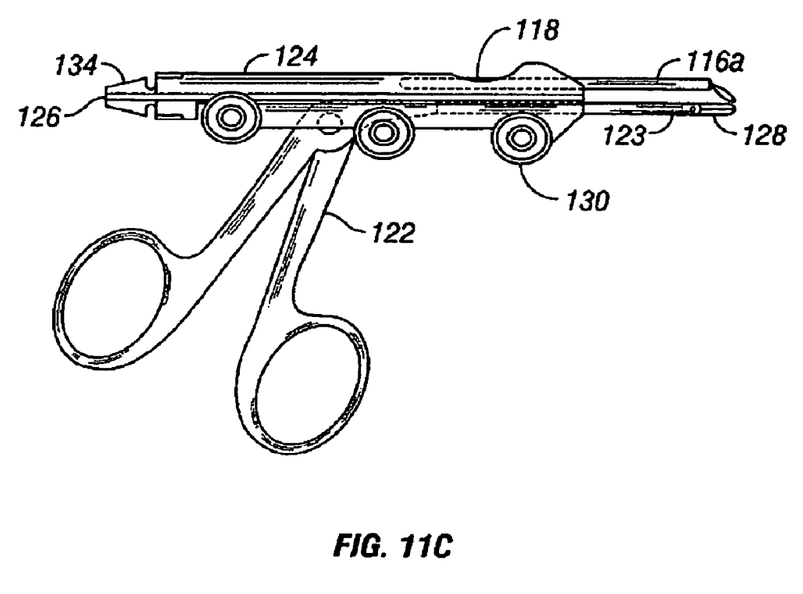
FIG. 11C is a side elevation view of the loop-type retrieval tool of FIG. 11A, but with the grab tool in a retracted position.
Figure 12A:
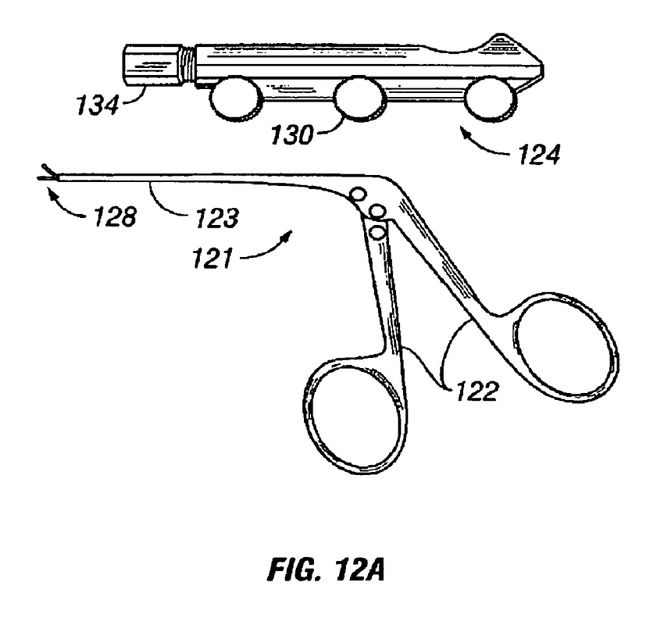
FIGS. 12A and 12B illustrate the relationship of the tool barrel and grab tool combination retrieval tool of FIGS. 11A to 11C.

FIGS. 11A to 11C illustrate an alternative grab-type retrieval tool 120 which is mountable on the fiberoptic cable 60 in the manner of a stop/handle 100, and which, like the stop/handle 100 is otherwise separate from the otoscope body 20. This grab-type retrieval tool 120 incorporates a separate grab tool 121 having a handle 122 and grab probe 123 (see FIG. 12A) and a tool barrel 124. In this preferred embodiment, the grab tool 121 was a commercially available mechanically operated forceps (Micro-ear Forceps, part no. 19-2081-B, Miltex, Inc. Bethpage, N.Y. & Tuttlingen, Germany). The grab tool 121 was received in a channel in the tool barrel 124, and held in position by the action of screw clamp means 130. The opposed jaws 128 of the grab tool 121 were manually operable to open and close by means of the scissor-type handles 122. Other grab tools 121 are known to and adaptable by the ordinary skilled artisan for practice in the present grab-type retrieval tool 120.

Figure 12B:
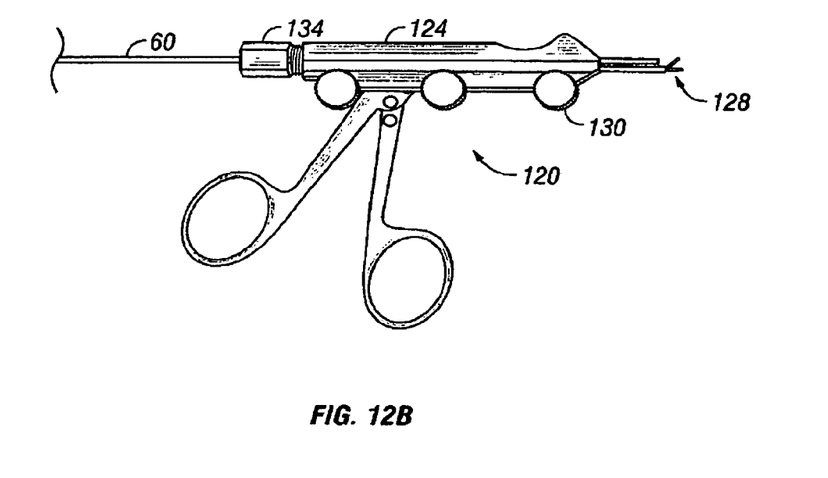
Figure 13:
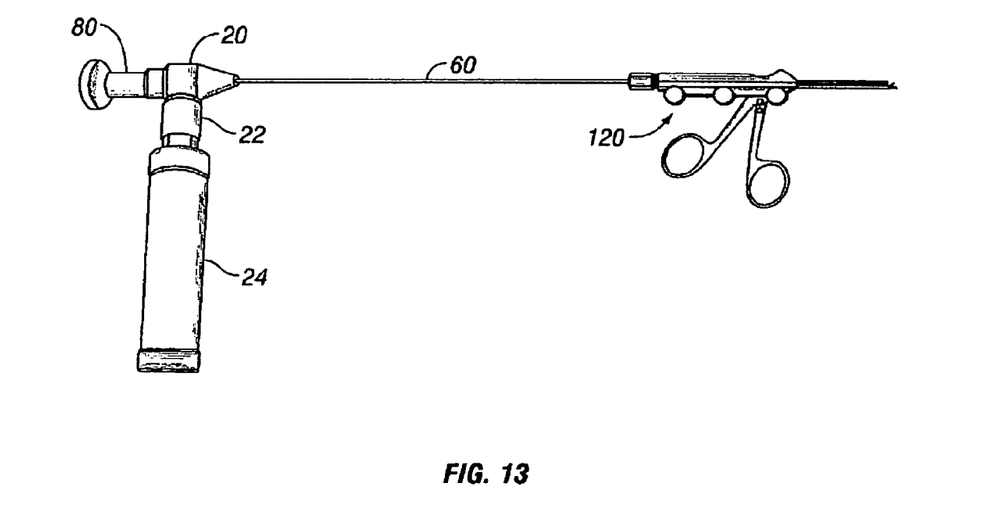
FIG. 13 is a representation of the present fiberoptic otoscope system with a retrieval tool fixed proximate the distal end of the fiberoptic cable.

The tool barrel 124 has a central bore 126 through which the fiberoptic cable 60 is passed to be proximate the jaws 128 of the grab tool 121 (see FIG. 12B). The fiberoptic cable was held in place in the barrel bore 126 by means of a swedge fitting 134 (partially shown). Generally, the distal end 63 of the fiberoptic cable 60 is positioned proximate the jaws 128 to illuminate and view the site at which the jaws 128 are to be operated. In the preferred embodiment illustrated, the tool barrel 124 also included a tool bore 117 for receiving (in the example shown) a loop-type retriever tool 116*a*. The retrieval tool 116*a* was manually positionable by means of a touch access 118 as described above. FIG. 13 is a representation of the present fiberoptic otoscope 10 with the grab-type retrieval tool 120 fixed proximate the distal end 63 of the fiberoptic cable 60.

Figure 14:
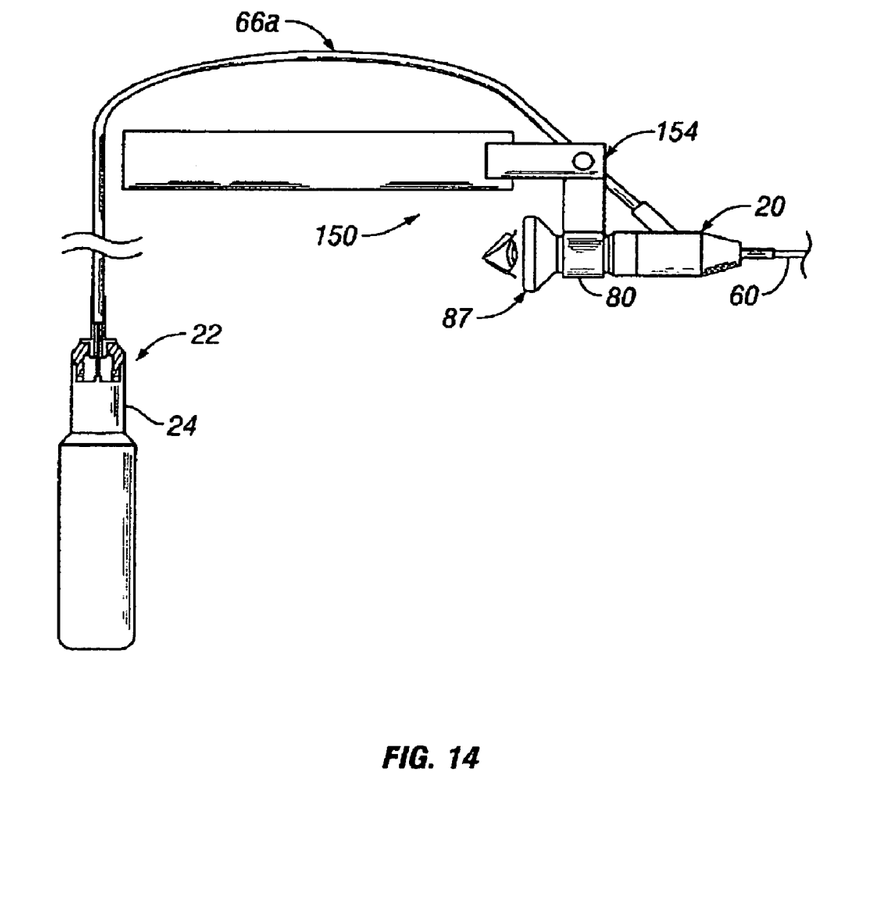
FIG. 14 illustrates the present fiberoptic otoscope system with the otoscope viewer and body mounted on a headband and connected to a remote light source via an auxiliary light path.

FIG. 14 illustrates a preferred embodiment of the present fiberoptic otoscope system in use. As shown in the illustration, the viewer 80 and body 20 of the present fiberoptic otoscope 10 is mounted on a headband 150. A detachable light source 24*a* is connected to the light source adapter 22 and is in light transmission communication with light path 66 of the fiberoptic cable 60 via a light path extension 66*a*. The auxiliary light path extension 66*a* allows the light source 24*a* to be remotely located relative to the fiberoptic otoscope 10 itself, if it is desired to utilize the full passive features of the device 10. The body and viewer combination 20 & 80 are mounted to the headband 150 via an articulated arm 154, which allows the eye piece 87 of the viewer 80 to be appropriately positioned by a user for viewing. The headband mounting system 150 frees a user's hands from having to hold the body and viewer combination 20 & 80 while using the present fiberoptic otoscope 10.

While the above description contains many specifics, these should not be construed as limitations on the scope of the invention, but rather as exemplifications of one or another preferred embodiment thereof. Many other variations are possible, which would be obvious to one skilled in the art. Also, Applicant wishes to thank Myriad Fiber Imaging Tech., Inc. of Dudley, Massachusetts for their technical assistance in producing prototype embodiments of the present invention.

What is claimed is:

1. A passive optical image viewing fiberoptie otoscope comprising an otoscope body, the otoscope body interfacing with a flexible solid fiberoptic cable, an achromatic optical image viewer, and a light source connector, in combination providing an achromatically corrected optical image, wherein:
    the otoscope body has a cable end, a viewer end and a mid-section, and has an interior passage connecting the cable end with the viewer end, and an intersecting passage through the mid section connecting to the interior passage;
    the flexible solid fiberoptic cable is in communication with the interior passage and extends out from the cable end of the otoscope body, the fiberoptic cable having a plurality of optical fibers for conducting light, wherein the solid fiberoptic cable comprises a light emitting path surrounding an image receiving path, the light emitting path being a plurality of light conduits closely packed and surrounding the image receiving path, and the image receiving path being a single image conduit and having a distal end abutting a lens complex adapted for receiving light;
    the achromatic optical image viewer attached to the viewer end of the otoscope body and in communication with the interior passage and an image receiving path for displaying a received light image for optical viewing by a user; and
    the light source connector attached to the mid-section of the otoscope body and in communication with the intersecting passage, the light source connector for attaching to an external light source.

2. The optical image viewing fiberoptic otoscope of claim 1, wherein the cable end of the otoscope body comprises a fiber optic cable head, the cable head for receiving and supporting the solid fiberoptic cable.

3. The optical image viewing fiberoptic otoscope of claim 2, wherein the cable end of the otoscope body comprises a fiber optic cable head integral to the otoscope body.

4. The optical image viewing fiberoptic otoscope of claim 1, wherein the solid fiberoptic cable has a first proximal end passing through the cable end and into the interior passage of the otoscope body, and a second distal end adapted for emitting and receiving light.

5. The solid fiberoptic cable of claim 4, wherein the solid fiberoptic cable comprises an exterior surface of the light path surrounding the image path being tightly encased in a polyamide coating.

6. The solid fiberoptic cable of claim 4, wherein the adaptation at the distal end of the fiberoptic cable for receiving light is selected from the group consisting of: a gradient index lens and a dual achromatic lens complex.

7. The solid fiberoptic cable of claim 4, wherein the distal end of the fiberoptic cable is covered by a removable, optically neutral septum.

8. The solid fiberoptic cable of claim 4, wherein the proximal end passes through the cable end into the interior passage and the image path and the light path diverge, with the image path proceeding through the interior passage to communicate with the achromatic optical image viewer and the light path proceeds through the intersecting passage to communicate with the light source connection.

9. The solid fiberoptic cable of claim 8, wherein the light path comprises a plurality of light conduits which terminates at the light source connection in a light path interface where the light path receives illuminating light from an external light source.

10. The optical image viewing fiberoptic otoscope of claim 1, wherein the achromatic optical image viewer comprises:
    an achromatic lens complex, the achromatic lens complex interfacing and in light communication with an image conduit disposed at the viewer end interior passage of the otoscope body, the image conduit communicating a received image to the achromatic lens complex and the achromatic lens complex processing the received image to provide color correction and image inversion and projecting the processed image through a focal chamber onto an eyepiece lens; and
    a focal chamber having a mounting end and an eyepiece end, the mounting end housing the achromatic lens complex and connecting to the otoscope body, the eyepiece end housing the eyepiece lens disposed to properly receive the processed image projected by the achromatic lens complex and display the processed image to a user.

11. The achromatic optical image viewer of claim 10, wherein the disposition of the eyepiece lens relative to the achromatic lens complex is adjustable to provide correction for the user's vision.

12. The optical image viewing fiberoptic otoscope of claim 1, further comprising a tool for performing an operation at a site proximate the distal end of the fiberoptic cable.

13. The optical image viewing fiberoptic otoscope of claim 1, further comprising a tool for engaging and removing a material at a site proximate the distal end of the fiberoptic cable.

14. The optical image viewing fiberoptic otoscope of claim 12, wherein the tool for performing an operation at a site proximate the distal end of the fiberoptic cable is attachable to the otoscope body.

15. The optical image viewing fiberoptic otoscope of claim 12, wherein the tool for performing an operation at a site proximate the distal end of the fiberoptic cable is attachable to the fiberoptic cable.

16. The optical image viewing fiberoptic otoscope of claim 13, wherein the tool is a retrieval tool selected from the group consisting of loop-type retrieval tools and grab-type retrieval tools.

17. The optical image viewing fiberoptic otoscope of claim 1, further comprising an auxiliary light source connector attachable to the light source connector for communicating with a remote external light source.

18. An optical image viewing fiberoptic otoscope system comprising the passive optical image viewing fiberoptic otoscope of claim 1; and a headband mounting system with an articulated support arm, the support arm having a distal mount means for attaching to the optical image viewing fiberoptic otoscope.

19. A passive optical image viewing fibcroptic otoscope comprising an otoscope body, interfacing with a flexible solid fiberoptic cable, an achromatic optical image viewer, and a light source connector, wherein:

the otoscope body, the fiberoptic cable, the achromatic optical image viewer, and the light source connector consist of non magnetic materials;

the otoscope body having a cable end, a viewer end and a mid-section, and an interior passage connecting the cable end with the viewer end, and an intersecting passage through the mid section connecting to the interior passage;

with the flexible solid fiberoptic cable in communication with the interior passage and extending out from the cable end of the otoscope body, the fiberoptic cable having a light emitting path, the light emitting path being a plurality of light conduits closely packed and tightly surrounding an image receiving path, and the image receiving path being a single image conduit having a distal image path end lens for receiving light, the lens being selected from the group consisting of a gradient index lens and a dual achromatic lens complex;

the achromatic optical image viewer being attached to the viewer end of the otoscope body and in communication with the interior passage and an image receiving path for displaying a received light image for optical viewing by a user, the achromatic optical image viewer having an achromatic lens complex interfacing and in light communication with an image conduit disposed at the viewer end interior passage of the otoscope body, the image conduit communicating a received image to the achromatic lens complex and the achromatic lens complex processing the received image to provide color correction and image inversion and projecting the processed image through a focal chamber onto an eyepiece lens, and the focal chamber having a mounting end and an eyepiece end, the mounting end housing the achromatic lens complex and connecting to thc otoscope body, the eyepiece end housing the eyepiece lens disposed to properly receive the processed image projected by the achromatic lens complex and display the processed image to a user, and the light source connector being attached to the mid-section of the otoscope body and in communication with the intersecting passage, the light source connector for attaching to an external light source.

\* \* \* \* \*